(12) United States Patent
Yamaguchi

(10) Patent No.: US 9,222,899 B2
(45) Date of Patent: Dec. 29, 2015

(54) X-RAY TALBOT INTERFEROMETER AND X-RAY IMAGING SYSTEM INCLUDING TALBOT INTERFEROMETER

(71) Applicant: CANON KABUSHIKI KAISHA, Tokyo (JP)

(72) Inventor: Kimiaki Yamaguchi, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 112 days.

(21) Appl. No.: 14/204,401

(22) Filed: Mar. 11, 2014

(65) Prior Publication Data
US 2014/0270061 A1  Sep. 18, 2014

(30) Foreign Application Priority Data
Mar. 12, 2013 (JP) .................... 2013-049349

(51) Int. Cl.
*G01N 23/20* (2006.01)
*G01J 9/02* (2006.01)
*G02B 5/18* (2006.01)
*G01B 9/02* (2006.01)

(52) U.S. Cl.
CPC ........ *G01N 23/20075* (2013.01); *G01B 9/0203* (2013.01); *G02B 5/1819* (2013.01); *G02B 5/1838* (2013.01); *G02B 5/1842* (2013.01); *G01J 9/02* (2013.01); *G01N 2223/04* (2013.01); *G01N 2223/05* (2013.01)

(58) Field of Classification Search
CPC ........ G01B 9/00; G01B 9/02; G01B 9/02029; G01B 9/0203; G01B 9/02041; G01B 9/0209; G01B 9/02091; G01B 9/021; G02B 5/00; G02B 5/18; G02B 5/1809; G02B 5/1814; G02B 5/1819; G02B 5/1823; G02B 5/1838; G02B 5/1842; G02B 5/1866; G02B 5/1871; G01J 9/00; G01J 9/02

USPC .............. 378/36, 70, 204, 210; 356/450, 457, 356/521; 359/1, 10, 11, 30, 32, 577, 580, 359/589, 590, 896, 902

See application file for complete search history.

(56) References Cited

U.S. PATENT DOCUMENTS

2010/0290590 A1* 11/2010 Ouchi .................... G06T 7/0002
378/62
2012/0093297 A1* 4/2012 Kondoh .................... G01D 5/38
D5/38
2013/0235973 A1* 9/2013 Murakoshi ........... A61B 6/4233
378/37

FOREIGN PATENT DOCUMENTS

JP   2011163937 A   8/2011
WO  2004058070 A1   7/2004

* cited by examiner

*Primary Examiner* — Anastasia Midkiff
(74) *Attorney, Agent, or Firm* — Canon USA Inc. IP Division

(57) ABSTRACT

An X-ray Talbot interferometer includes a first grating configured to diffract X-rays from an X-ray source and form an interference pattern, a second grating configured to block a portion of X-rays that form the interference pattern, and a detector configured to detect X-rays from the second grating. An inspection object is disposed between the X-ray source and the second grating. The second grating includes a first shield grating portion in which a shield portion and a transmissive portion are arranged periodically at a first period and a second shield grating portion. The first period is expressed as $ps \times n \times Ls/(Ls+Lf)$, where ps denotes a size of pixels that the detector has, n denotes a positive integer, Ls denotes a distance from the X-ray source to the first shield grating portion, and Lf denotes a distance from the first shield grating portion to the detector.

17 Claims, 9 Drawing Sheets

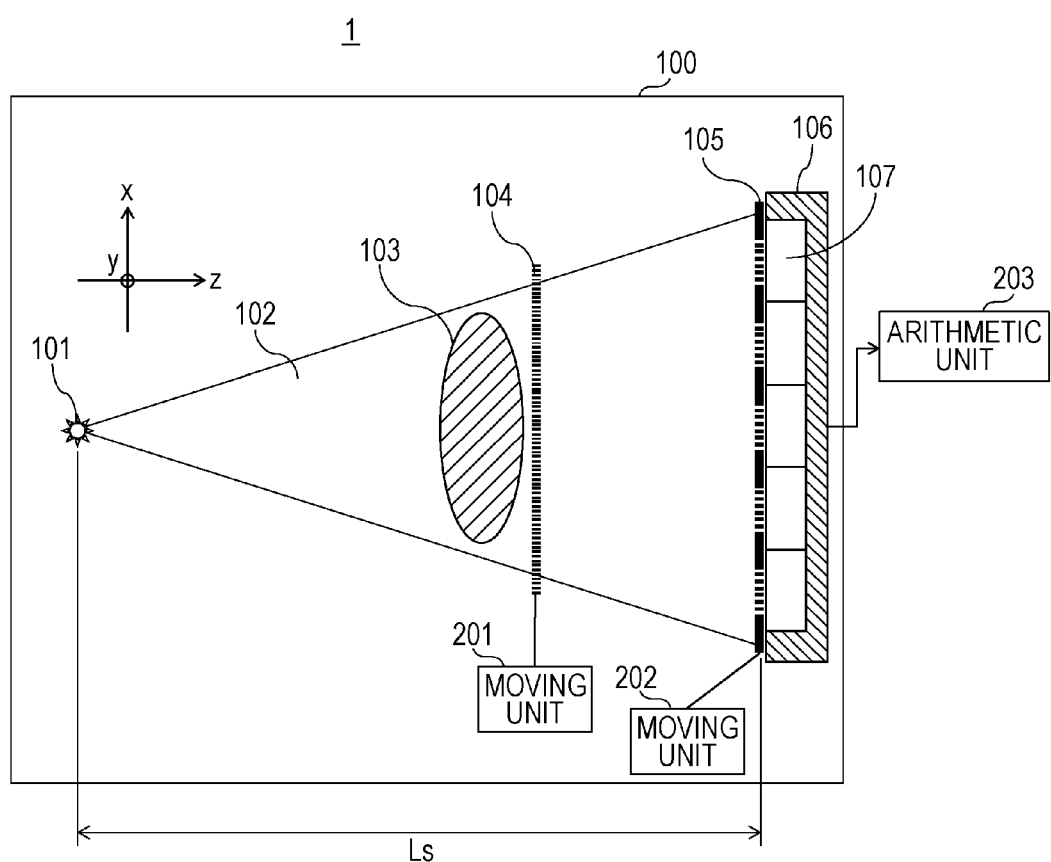

X-RAY TALBOT INTERFEROMETER AND X-RAY IMAGING SYSTEM INCLUDING TALBOT INTERFEROMETER

BACKGROUND OF THE INVENTION

1. Field of the Invention

The present invention generally relates to radiative energy, and in particular it relates to an X-ray Talbot interferometer and an X-ray imaging system equipped with a Talbot interferometer.

2. Description of the Related Art

Recently, an image capturing method called X-ray phase contrast imaging has been studied in which contrast is generated on the basis of a phase change of X-rays caused by the X-rays passing through an inspection object. As an example of X-ray phase contrast imaging, an image capturing method called X-ray Talbot interferometry using Talbot interference has been described in International Publication No. WO04/058070.

An overview of a Talbot interference method will be described. In a Talbot interference method, an X-ray Talbot interferometer is generally used that includes a diffraction grating, a shield grating, and a detector configured to detect X-rays from the shield grating. When the diffraction grating is irradiated with spatially high coherence X-rays, such X-rays are diffracted by the diffraction grating and form an interference pattern (which may also be called a self-image) that has a brightness period at specific positions (the Talbot effect). Generally, the period of this self-image is smaller than the size of pixels of the detector. Thus, a portion of the self-image is blocked by the shield grating, a periodic pattern with a wider pitch is formed, and this periodic pattern is detected by the detector.

When an inspection object is arranged between an X-ray source and the detector, X-rays from the X-ray source are refracted, absorbed, and scattered by the inspection object. As a result, the self-image is changed and a periodic pattern formed by the self-image and the shield grating is also changed. Information on the inspection object may be obtained by detecting this periodic pattern by using the detector and, if necessary, by performing calculation using a detection result.

SUMMARY OF THE INVENTION

An X-ray Talbot interferometer according to an aspect of the present invention includes a first grating configured to diffract X-rays from an X-ray source and form an interference pattern, a second grating configured to block a portion of X-rays that form the interference pattern, and a detector configured to detect X-rays from the second grating. A property of an inspection object disposed between the X-ray source and the second grating is measured. The second grating includes a first shield grating portion in which a shield portion and a transmissive portion are arranged periodically at a first period and a second shield grating portion in which a shield portion and a transmissive portion are arranged periodically at a second period. The first period is expressed as follows:

$$ps \times n \times \frac{Ls}{Ls + Lf}$$

where ps denotes a size of pixels that the detector has, n denotes a positive integer, Ls denotes a distance from the X-ray source to the first shield grating portion, and Lf denotes a distance from the first shield grating portion to the detector.

Further features of the present invention will become apparent from the following description of exemplary embodiments with reference to the attached drawings.

BRIEF DESCRIPTION OF THE DRAWINGS

FIG. 1 is a schematic diagram of an X-ray imaging system including an X-ray Talbot interferometer according to a first embodiment.

DESCRIPTION OF THE EMBODIMENTS

Figure 2A:
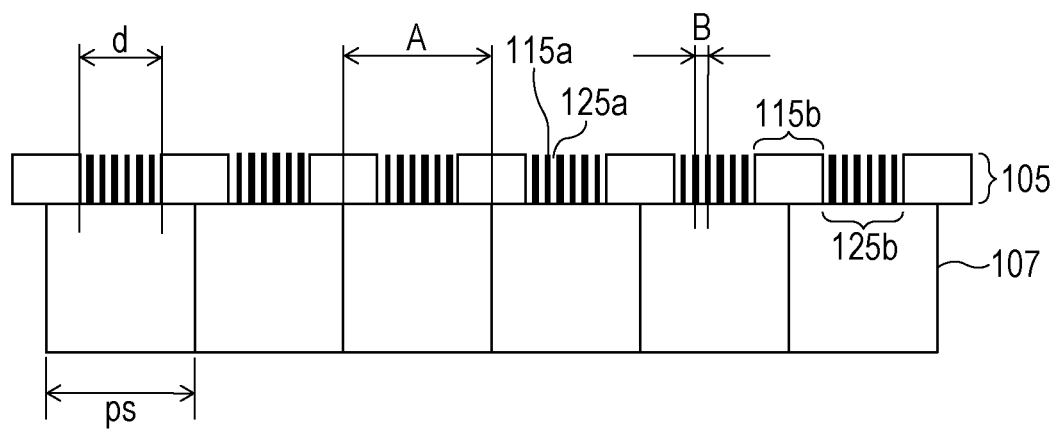
FIG. 2A is a schematic diagram of a second grating according to the first embodiment.

In the following, preferred embodiments of the present invention will be described with reference to attached drawings. Note that, in each of the drawings, the same members are denoted by the same reference numerals and redundant description will be omitted.

When a pattern formed by an interference pattern and a shield grating is detected by a detector, the visibility of a detection result may be decreased by the effect of a modulation transfer function (MTF) of the detector. "Visibility" means the contrast of a moiré pattern. In addition, digital X-ray detectors are often used with X-ray Talbot interferometers, and the visibility of a detection result may be decreased by the effect of a sampling frequency in the case where a digital X-ray detector is used.

In the embodiments described herein, an X-ray Talbot interferometer may realize higher visibility for a detection result obtained by a detector than conventional imaging devices.

An X-ray Talbot interferometer according to an embodiment includes a first grating, which is a diffraction grating, and a second grating, which is a shield grating. The first grating diffracts X-rays and forms an interference pattern. The second grating blocks a portion of X-rays that form the interference pattern formed by the first grating. Furthermore, the X-ray Talbot interferometer includes a detector configured to detect X-rays from the second grating, and information on a periodic pattern formed by the interference pattern and the second grating is detected by the detector. An X-ray imaging system may be configured by using, in combination, this X-ray Talbot interferometer and an arithmetic unit that calculates information on an inspection object by using a detection result obtained from the detector.

The second grating includes a first shield grating portion in which a shield portion and a transmissive portion are arranged at a first period, and a second shield grating portion in which a shield portion and a transmissive portion are arranged at a second period.

The first shield grating portion may be a two-dimensional grating that has a two-dimensional pattern that has periods in two directions. In such a case, the first shield grating portion may be a two-dimensional pattern that has the first period in the x direction and a third period in the y direction, which intersects with the x direction. Alternatively, the first shield grating portion may have the first period in both the x and y directions. This similarly applies to the second shield grating portion.

When the distance between the first shield grating portion and the detector is 0, a first period A that the first shield grating portion has is an integral multiple (n times) of a pixel size ps of the detector in the direction of the first period. When the distance between the first shield grating portion and the detector is other than 0, a first period obtained when the first shield grating portion is projected onto the detector is adjusted so as to be an integral multiple of the pixel size ps of the detector in the direction of the first period. Accordingly, the first period A is adjusted in accordance with the distance between the first shield grating portion and the detector.

The visibility of a detection result may be increased by adjusting an aperture ratio D of the first shield grating portion. As used herein, the aperture ratio D=the width of a transmissive portion/(the width of a transmissive portion+the width of a shield portion). Here, the width of the transmissive portion and the width of the shield portion refer to the width of a transmissive portion and the width of a shield portion in the direction of the first period (direction of periodicity). Note that the higher the aperture ratio of the first shield grating portion, the greater the amount of X-rays per unit time with which the detector is irradiated. A case where a fixed amount of X-rays that enter the detector regardless of the aperture ratio D will be described in a first embodiment, and a case where the smaller the aperture ratio D, the smaller the amount of X-rays that enter the detector will be described in a second embodiment (for example, a fixed amount of X-rays enter an inspection object regardless of the aperture ratio D).

The second shield grating portion has only to be configured such that a periodic pattern (a moiré pattern) is formed on the detector by blocking a portion of an interference pattern in a periodic manner. Thus, the second period that the second shield grating portion has is generally smaller than the pixel size in the direction of the second period.

Note that an X-ray Talbot interferometer of an embodiment is not limited to an X-ray Talbot interferometer that obtains an image of an inspection object; it is sufficient that the X-ray Talbot interferometer is capable of and configured to measure a property of the inspection object, for example, by detecting an intensity distribution of a periodic pattern formed by X-rays the phase and intensity of which have been changed by the inspection object.

In the following sections, the present invention will be described in more detail with reference to non-limiting embodiments.

First Embodiment

FIG. 1 is a schematic diagram illustrating the configuration of an X-ray Talbot interferometer 100 of the first embodiment. The X-ray Talbot interferometer 100 illustrated in FIG. 1 includes a first grating 104 and a second grating 105. The first grating 104 forms an interference pattern by diffracting X-rays 102 from an X-ray source 101. The second grating 105 blocks a portion of X-rays of the interference pattern formed by the first grating 104. Furthermore, the X-ray Talbot interferometer 100 includes a detector 106 and moving units 201 and 202. The detector 106 detects X-rays from the second grating 105. The moving units 201 and 202 cause the first grating 104 and the second grating 105 to move respectively and independently from each other. An X-ray imaging system 1 includes the X-ray Talbot interferometer 100, an arithmetic unit 203, and the X-ray source 101. An inspection object 103 is arranged between the X-ray source 101 and the first grating 104. The arithmetic unit 203 is operatively connected to the detector 106, and calculates information on the inspection object 103 on the basis of a detection result of the detector 106. The X-ray source 101 irradiates the first grating 104 with X-rays. Note that, in FIG. 1, although the inspection object 103 is arranged between the X-ray source 101 and the first grating 104, the inspection object 103 may be arranged between the X-ray source 101 and the detector 106. Thus, the inspection object 103 may also be arranged between the first grating 104 and the second grating 105. In other words, in order from the x-ray source 101 to the first grating 104 and to the second grating 105, the inspection object 103 may be arranged anywhere between the x-ray source 101 and the second grating 105, before or after the first grating 104.

The first grating 104 may form an interference pattern by diffracting X-rays. For example, the first grating 104 may be a phase modulation grating that modulates the phase of X-rays in a periodic manner or an intensity modulation grating that modulates the intensity of X-rays in a periodic manner.

Figure 8A:
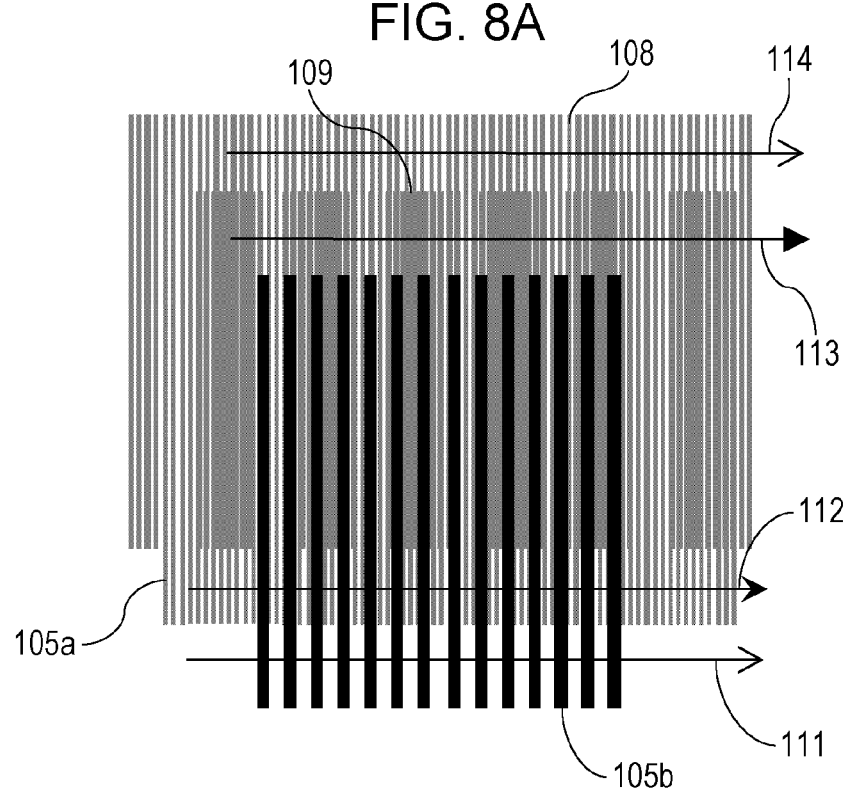
FIG. 8A is a schematic diagram of an interference pattern, a moiré pattern, and a direction of the period of the second grating associated with an exemplary embodiment 1 and an exemplary embodiment 2 of the present invention.
Figure 8B:
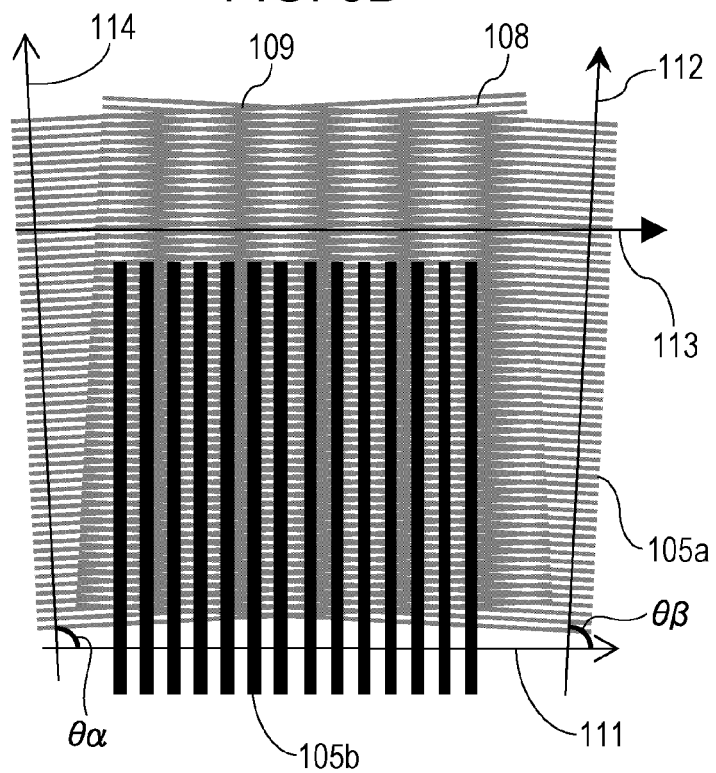
FIG. 8B is a schematic diagram of an interference pattern, a moiré pattern, and a direction of the period of the second grating associated with the exemplary embodiment 1 and the exemplary embodiment 2 of the present invention.

The second grating 105 is a shield grating that includes a first shield grating portion 105b and a second shield grating portion 105*a* (see FIGS. 8A and 8B). The second grating 105 is arranged at a position where the interference pattern is formed (at the Talbot distance). The first shield grating portion 105*b* and the second shield grating portion 105*a* are arranged in a periodic manner, such that the second grating 105 blocks, in a periodic manner, a portion of X-rays that form the interference pattern. In this manner, the second grating 105 forms a periodic pattern having a shape different from that of the interference pattern formed by the first grating 104.

Figure 2B:
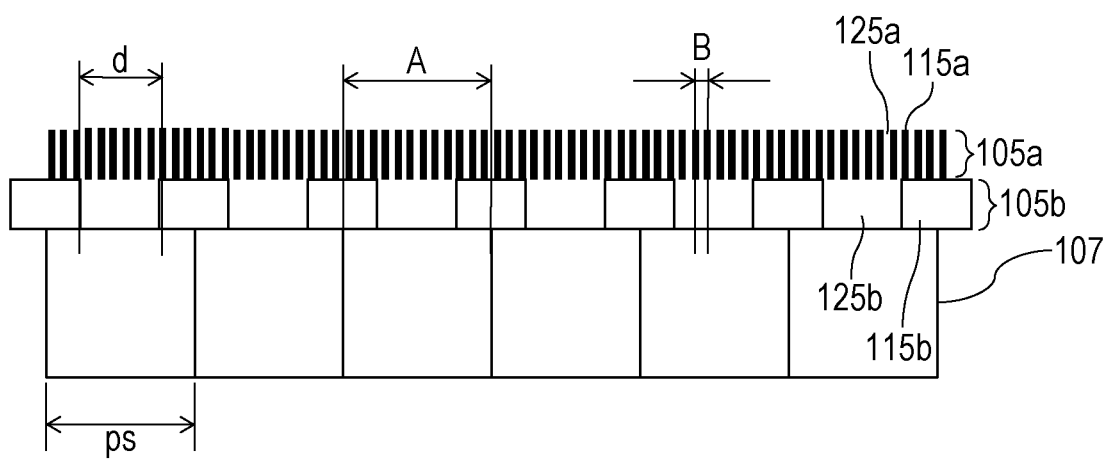
FIG. 2B is a schematic diagram of a second grating according to the first embodiment.

In the first shield grating portion 105*b*, a shield portion 115*b* and a transmissive portion 125*b* are arranged at a first period A. In the second shield grating portion 105*a*, a shield portion 115*a* and a transmissive portion 125*a* are arranged at a second period B. Note that the first shield grating portion 105*b* and the second shield grating portion 105*a* may be integrally configured as illustrated in FIG. 2A. Alternatively, the first shield grating portion 105*b* and the second shield grating portion 105*a* may be configured independently from each other as illustrated in FIG. 2B. In addition, the width of the transmissive portion 125*b* of the first shield grating portion 105*b* may also be called an aperture of width d. As illustrated in FIG. 2A, in the case where the first shield grating portion 105*b* and the second shield grating portion 105*a* are integrally configured, shield portions 115*a* and transmissive portions 125*a* of the second shield grating portion 105*a* are formed in a transmissive portion 125*b* of the first shield grating portion 105*b*. A shield portion 115*b* of the first shield grating portion 105*b* is formed in some of transmissive portions 125*a* of the second shield grating portion 105*a*. In addition, as shown in FIG. 2B, in the case where the first shield grating portion 105*b* and the second shield grating portion 105*a* are configured independently from each other, the first shield grating portion 105*b* may be coupled (but does not need to be coupled) to the second shield grating portion 105*a*. In addition, either of the second shield grating portion 105*a* and the first shield grating portion 105*b* may be arranged to be nearer to the detector 106. Note that when the first shield grating portion 105*b* is positioned away from the detector 106, the effect of improving the MTF is decreased. On the basis of this, it is desirable that the first shield grating portion 105*b* be positioned near to pixels 107 of the detector 106 (as shown in FIG. 2B).

The first period A, which the first shield grating portion 105*b* has, is n times the pixel size ps (A=ps×n). In the case where it is not possible to make the distance between the first shield grating portion 105*b* and the detector 106 be 0, the first period A needs to be adjusted using the following expression.

$$A = ps \times n \times \frac{Ls}{Ls + Lf}$$

Note that Ls denotes the distance from the X-ray source 101 to the first shield grating portion 105*b* and Lf denotes the distance from the first shield grating portion 105*b* to the detector 106.

In this manner, when the first period A is corrected in accordance with the distance between the first shield grating portion 105*b* and the detector 106, the first period A to be projected onto the detector 106 may be n times the pixel size ps. Since Ls/(Ls+Lf)=1 when the distance between the first shield grating portion 105*b* and the detector 106 is 0, the first period A is n times the pixel size ps (A=ps×n). In FIG. 1, Lf is not illustrated because Lf=0.

Note that, in FIGS. 2A and 2B, since the first period A=the pixel size (ps), n=the first period A/the pixel size=1.

In addition, the shield portions 115*b* and 115*a* need not be able to completely block incident X-rays. It is preferable that the shield portions 115*b* and 115*a* be configured to or capable of blocking 90% or more of X-rays that have entered at right angles with respect to the shield portions 115*b* and 115*a*.

The first shield grating portion 105*b* improves the visibility of a detection result by blocking a portion of X-rays that form an interference pattern. The relationship between an aperture ratio and the visibility of a detection result will be described in detail further below.

The second shield grating portion 105*a* forms, on the detector 106, a periodic pattern different from that of an interference pattern by blocking a portion of X-rays that form the interference pattern. That is, the second shield grating portion 105*a* realizes a function similar to that of a shield grating (also called an absorption grating, a second diffraction grating, or the like) in general X-ray Talbot interferometers.

In the case where the second period B slightly differs from the period of an interference pattern, an enlarged or reduced moiré pattern, which is a type of moiré pattern, is formed on the detector 106 in accordance with the difference between the periods. In addition, even when the second period B is the same as the period of the interference pattern, in the case where the direction of the second period B intersects with that of the period of the interference pattern, a rotation moiré pattern, which is a type of moiré pattern, is formed on the detector 106 in accordance with an angle formed by the directions. In addition, in the case where the second period B is the same as the period of the interference pattern and the direction of the second period B matches that of the period of the interference pattern, a periodic pattern the period of which is the same as the period of interference pattern is formed on the detector 106. However, unless bright portions of the interference pattern are formed such that the positions of the bright portions completely match the positions of transmissive portions 125*a* of the second shield grating portion 105*a* and dark portions of the interference pattern are formed such that the positions of the dark portions completely match the positions of shield portions 115*a* of the second shield grating portion 105*a*, a periodic pattern that has a shape different from that of the interference pattern is formed on the detector 106. In this manner, even when the periodic pattern has the same period as the interference pattern, if the shape (the width of the dark portions or the like) corresponding of the periodic pattern differs from that of the interference pattern, the periodic pattern is treated as a periodic pattern different from the interference pattern.

The detector 106 is a digital X-ray detector and includes a plurality of pixels 107. The pixels 107 may be arranged in a one-dimensional array, in which pixels are arranged in one direction adjacent to each other. Preferably, the pixels 107 are arranged in a two-dimensional array (matrix), in which pixels are arranged in two directions (rows and columns), in order to widen a measurable range.

The relationship between the aperture ratio of the first shield grating portion 105*b* and the visibility of a detection result will be described.

In the first embodiment, regardless of the aperture ratio of the first shield grating portion 105*b* that the second grating 105 has, an inspection object is irradiated with a constant amount of X-rays and is measured. To this end, an exposure time or the output of the X-ray source 101 may be changed in accordance with the aperture ratio of the second grating 105. In addition, in order to simplify calculation, each of the first grating 104 and the second shield grating portions 105b and 105a of the second grating 105 is, here, a one-dimensional grating having a one-dimensional pattern that has a period in one direction.

Figure 3A:
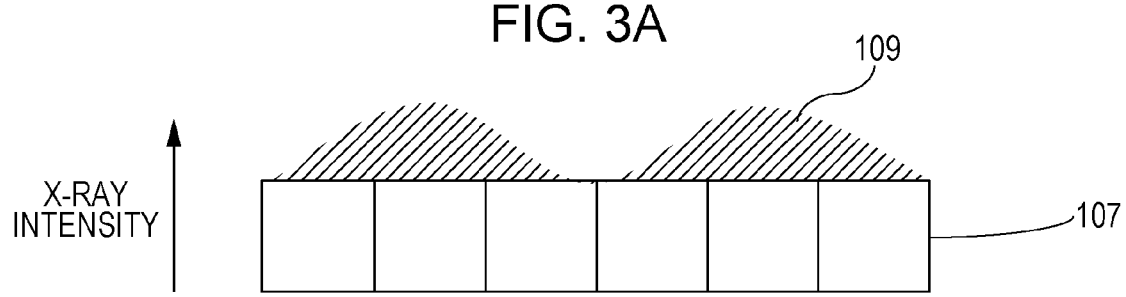
FIG. 3A is a schematic diagram illustrating a relationship between a moiré pattern and pixels according to the first embodiment.
Figure 3B:
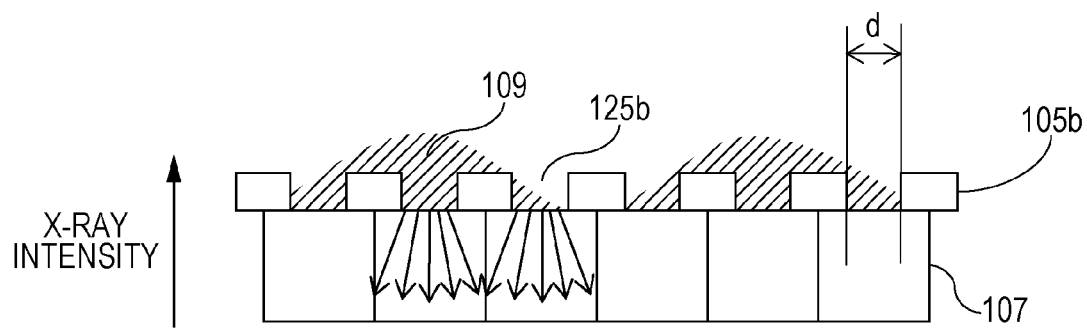
FIG. 3B is a schematic diagram illustrating a relationship between the moiré pattern, a first shield grating portion, and pixels of a detector according to the first embodiment.
Figure 3C:
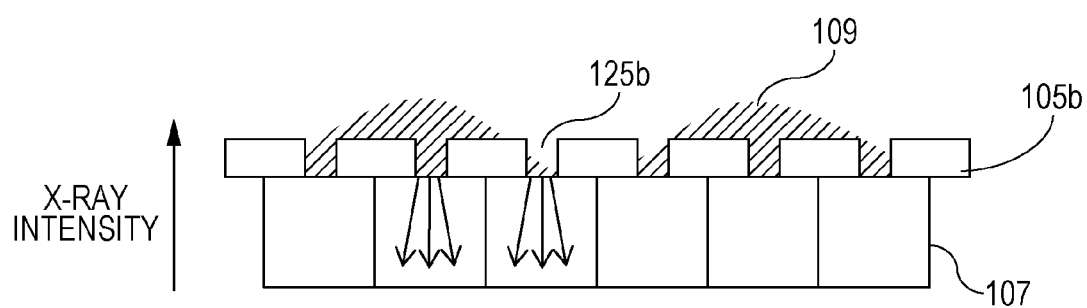
FIG. 3C is a schematic diagram illustrating a relationship between the moiré pattern, the first shield grating portion, and the pixels according to the first embodiment.

For description of the first embodiment, FIGS. 3A to 3C are schematic diagrams illustrating a relationship between a moiré pattern 109 generated by a self-image and the second shield grating portion 105a, pixels 107, and the first shield grating portion 105b. Note that the moiré pattern 109 shows that the X-ray intensity becomes higher toward a peak of a mountain-like curve and lower toward the bottom of the mountain-like curve.

FIG. 3A illustrates a case where the aperture ratio of the first shield grating portion 105b is 100%, that is, the second grating 105 has no first shield grating portion 105b. This matches the relationship between a moiré pattern and pixels in conventional X-ray Talbot interferometry described also in International Publication No. WO04/058070. In contrast, FIGS. 3B and 3C are schematic diagrams obtained when the first shield grating portion 105b is arranged between the moiré pattern 109, which is generated by the self-image and the second shield grating portion 105a, and the pixels 107.

The relationship between the aperture ratio and the visibility of a detection result is calculated.

The visibility of a detection result obtained when the moiré pattern 109 is obtained as digital data is defined as the following expression (0).

$$\text{Visibility} = F^{-1}(F(V\_m) \times F(MTF\_D)) \quad \text{Expression (0)}$$

V_m of Expression (0) denotes visibility of the moiré pattern 109 that has passed through the second grating 105. MTF_D denotes an amplitude modulation factor obtained when an aperture ratio (D) of the second grating 105 is changed. F denotes Fourier transform of each element, and $F^{-1}$ denotes inverse Fourier transform of each element.

When the number of periods of the moiré pattern 109 formed on the detector 106 (periods in a certain direction) is one, the visibility of Expression (0) may be expressed as Expression (1) below.

$$\text{Visibility} = V\_m \times MTF\_D \quad \text{Expression (1)}$$

In order to describe the first embodiment, the visibility may be expressed as Expression (1). In order to obtain the visibility of a detection result, V_m and MTF_D are calculated in the following.

First, V_m is calculated. The visibility V_m of the moiré pattern 109 is defined as in the following.

$$V\_m = \frac{V_{max} - V_{min}}{V_{max} + V_{min}}$$

Vmax and Vmin are calculated.

Here, the moiré pattern 109 is expressed as Expression (2) below.

$$\text{Moiré pattern} = f(x) = \frac{(\sin x + 1)}{2} \quad \text{Expression (2)}$$

When the period of the moiré pattern 109 on the detector 106 is m times the size ps of the pixels 107, Vmax and Vmin are expressed as follows.

$$V_{max} = \int_A^B f(x)\,dx, \ A = \frac{\pi}{2} - \frac{\pi}{2} \times \frac{2D}{m}, \ B = \frac{\pi}{2} + \frac{\pi}{2} \times \frac{2D}{m}$$

$$V_{min} = \int_C^E f(x)\,dx, \ C = \frac{3\pi}{2} - \frac{\pi}{2} \times \frac{2D}{m}, \ E = \frac{3\pi}{2} + \frac{\pi}{2} \times \frac{2D}{m}$$

Thus, the visibility V_m of the moiré pattern 109 is expressed as Expression (3).

$$V_m = \frac{V_{max} - V_{min}}{V_{max} + V_{min}} = \frac{m}{\pi D} \sin\frac{\pi D}{m} \quad \text{Expression (3)}$$

Next, MTF_D is calculated.

The pixels 107, which the detector 106 has, are discretely scattered, and the following expressions are satisfied.

$$\frac{\theta}{X} = \int_{X1}^{X2} f(x)\,dx, \ X1 = x0 - \frac{d}{2}, \ X2 = x0 + \frac{d}{2}$$

$$\frac{\theta}{X} = \frac{1}{2}\left(1 + \frac{\sin\frac{d}{2}}{\frac{d}{2}} \sin x0\right)$$

When the pixel size is denoted by ps, the relationship between the aperture width d and the aperture ratio D is expressed as d=D·m·ps/n. Thus, MTF_D is expressed as Expression (4) below.

$$MTF\_D = \frac{\sin\left(D \times m \times \frac{ps}{2n}\right)}{D \times m \times \frac{ps}{2n}} \quad \text{Expression (4)}$$

In accordance with Expressions (1) and (4), Expression (5) below is satisfied.

$$\text{Visibility} = V_m \times \frac{\sin(D \times m \times ps/2n)}{D \times m \times ps/2n} \quad \text{Expression (5)}$$

In addition, when the moiré pattern 109 is expressed as Expression (2), Expression (6) below is satisfied in accordance with Expressions (3) and (5).

$$\text{Visibility} = \frac{m}{\pi D} \sin\frac{\pi D}{m} \times \frac{\sin(D \times m \times ps/2n)}{D \times m \times ps/2n} \quad \text{Expression (6)}$$

Figure 4:
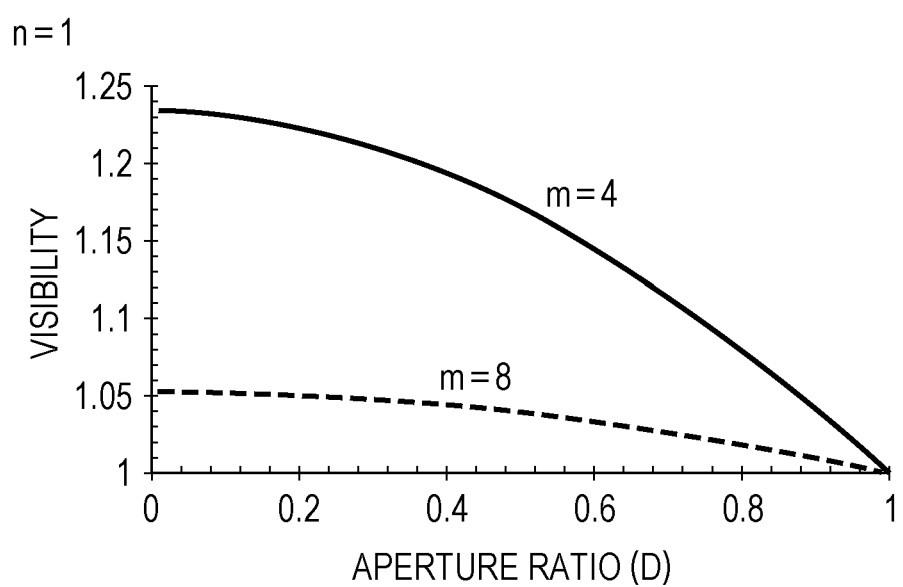
FIG. 4 is a graph illustrating a relationship between the visibility of a detection result and the aperture ratio of the first shield grating portion according to the first embodiment.

Results of calculation obtained when relationships between the aperture ratio D and the degree of improvement in visibility are calculated by substituting m=4 and m=8 into Expression (6) are illustrated in FIG. 4. The case where the aperture ratio D=1 refers to a state in which there is no first shield grating portion 105b. In addition, the degree of improvement in visibility represented by the vertical axis of FIG. 4 refers to visibility at each aperture ratio in the case where the visibility obtained when D=1 is standardized to 1.

As is clear from FIG. 4, in the first embodiment, the smaller the aperture ratio, the higher the degree of improvement in the visibility of the moiré pattern 109. Thus, it is clear that the visibility of a detection result may be improved by using the first shield grating portion 105b. In addition, in the case where information on an inspection object is calculated using a detection result as in the first embodiment, the amount of blurring of a periodic pattern contained in the detection result is decreased. Thus, information on the inspection object may be more precisely calculated. Thus, in the case where an image based on the calculation result is displayed, an artifact may be reduced or the contrast may be improved.

In the first embodiment, although each of the first grating 104 and the first and second shield grating portions 105b and 105a of the second grating 105 is a one-dimensional grating having a one-dimensional stripe-shaped pattern, each of the first grating 104 and the first and second shield grating portions 105b and 105a of the second grating 105 may be a two-dimensional grating that has periods in two directions that intersect with each other (the x direction and the y direction). In the case where two-dimensional gratings are used, the relationship between the aperture ratio ($D_y$, $D_y$) and the visibility of a detection result may be obtained by considering Expressions (1) and (4) in each of the x direction and the y direction.

Figure 5A:
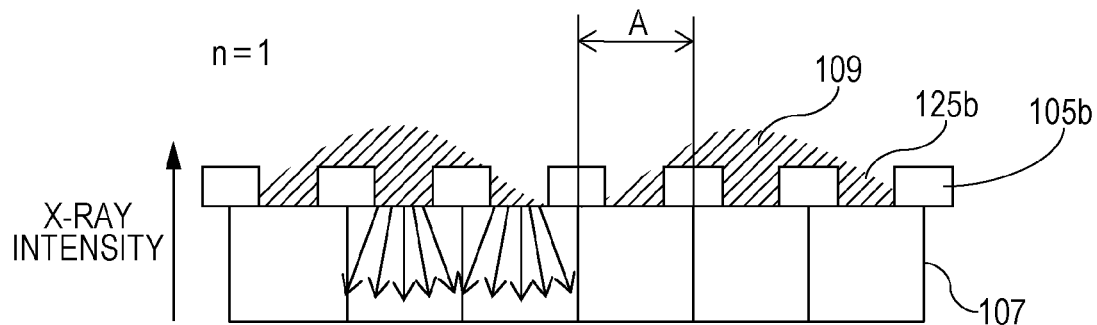
FIG. 5A is a schematic diagram of the moiré pattern and the first shield grating portion according to the first embodiment and a second embodiment.
Figure 5B:
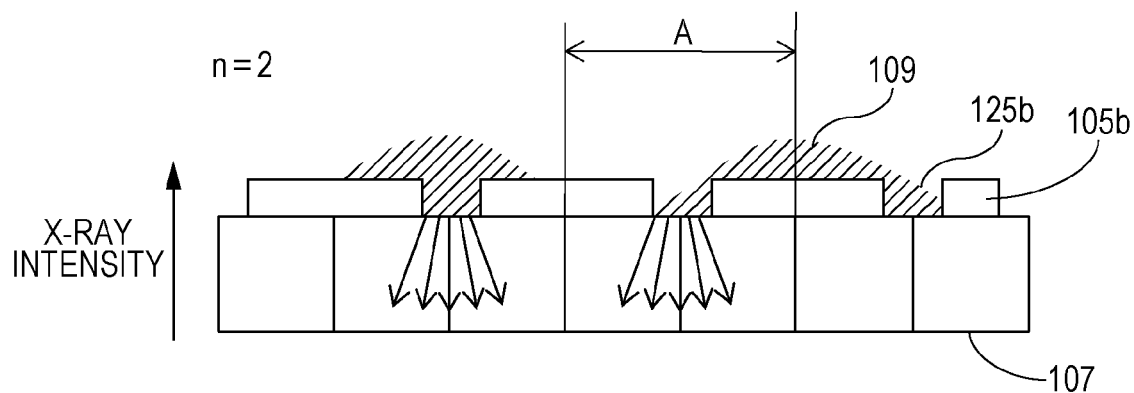
FIG. 5B is a schematic diagram of the moiré pattern and the first shield grating portion according to the first embodiment and the second embodiment.
Figure 5C:
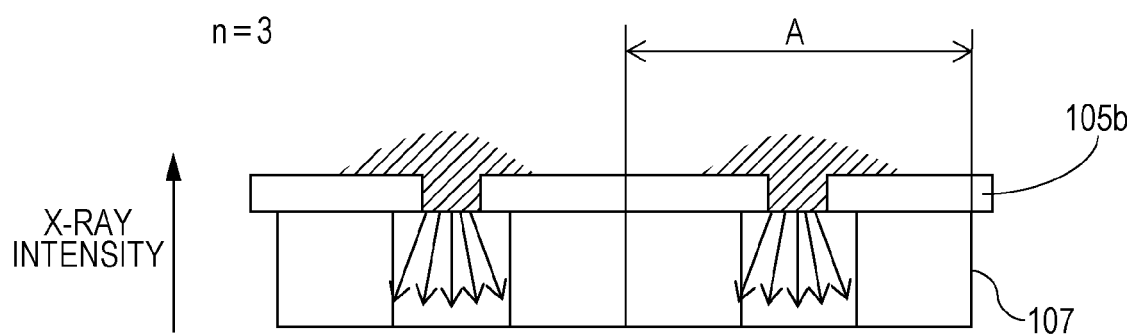
FIG. 5C is a schematic diagram of the moiré pattern and the first shield grating portion according to the first embodiment and the second embodiment.

Although the case where n=1 has been mainly described, as illustrated in FIGS. 5A to 5C, n may be a positive integer other than 1 in the first embodiment. As illustrated in FIG. 5C, when n≠1, there may be a pixel on which it is incapable of arranging a transmissive portion 125b of the first shield grating portion 105b, but this is also acceptable.

Note that although the case where the moiré pattern 109 is formed on the detector 106 has been described in the first embodiment, the first embodiment may also be similarly applied to a case where a periodic pattern other than a moiré pattern is formed.

The arithmetic unit 203 may calculate information on an inspection object by performing various types of calculation using a detection result of the detector 106. Information on an inspection object to be calculated and an arithmetic method are not specifically specified. Examples of information on an inspection object to be calculated include information regarding the X-ray transmittance (X-ray absorptivity) of the inspection object, information regarding X-ray scattering power of the inspection object, and information regarding X-ray phase change caused by the inspection object (hereinafter also referred to as phase information).

Examples of a method for calculating phase information on an inspection object include a method using Fourier transform (hereinafter also referred to as a Fourier transform method) in addition to a fringe scanning method described in International Publication No. WO04/058070. A Fourier transform method is, for example, described in Japanese Unexamined Patent Application Publication No. 2011-163937 and thus description of its details is omitted. In general, in a Fourier transform method, a periodic pattern the period of which is longer than that of a periodic pattern detected in a fringe scanning method is often used. Accordingly, the visibility of a periodic pattern used in a Fourier transform method tends to be decreased more significantly than that of a periodic pattern used in a fringe scanning method, due to the effect of the MTF of a detector. In addition, the frequency of a periodic pattern used in a Fourier transform method is closer to the sampling frequency of a detector than the frequency of a periodic pattern used in a fringe scanning method and the visibility of a detection result tends to be more significantly decreased in the Fourier transform method. Thus, the X-ray Talbot interferometer in which the first shield grating portion 105b is used as in the first embodiment may have a superior effect by being used together with an arithmetic unit that calculates information on an inspection object in a Fourier transform method.

Second Embodiment

As described in the first embodiment, when the aperture ratio of the first shield grating portion 105b is reduced, the visibility of a detection result is improved. However, in the case where the amount of X-rays with which the detector 106 is irradiated decreases with an decrease in the aperture ratio of the first shield grating portion 105b, the decrease in the aperture ratio causes an amount of noise to an X-ray intensity signal to increase. Thus, in the case where the amount of X-rays with which the detector 106 is irradiated decreases in accordance with a decrease in the aperture ratio of the first shield grating portion 105b, it is desirable that the aperture ratio of the first shield grating portion 105b is determined by considering the ratio (SNR) of noise power and X-ray intensity signal power. The case where the amount of X-rays with which the detector 106 is irradiated decreases with a decrease in the aperture ratio of the first shield grating portion 105b refers to a case where, for example, an exposure time is one second when the aperture ratio D=1 and the exposure time is shorter than two seconds when the aperture ratio D=0.5. In the second embodiment, a case will be described where SNR is considered in a Talbot interferometer in which the amount of X-rays with which the detector 106 is irradiated decreases with a decrease in the aperture ratio of the first shield grating portion 105b.

Each of the first grating 104 and the first and second shield grating portions 105b and 105a of the second grating 105 is a one-dimensional grating having a one-dimensional stripe-shaped pattern, and the X-ray transmittance of shield portions of the first shield grating portion 105b is 0. In the case where noise is only due to X-ray quantum noise and in the case where an amount of X-rays with which the inspection object 103 is irradiated is constant (that is, in the case where the aperture ratio D of the first shield grating portion 105b is proportional to an amount of X-rays with which irradiation is performed), the SNR obtained when D=0.5 is about 30% lower than the SNR obtained when D=1. Likewise, the SNR obtained when D=0.25 is 50% lower than the SNR obtained when D=1. In accordance with this, on condition that an amount of X-rays with which the inspection object 103 is irradiated is constant, it is desirable that the first shield grating portion 105b be designed by considering occurrence of a "phenomenon in which visibility improves" and also considering occurrence of a "phenomenon in which SNR decreases" as a result of reducing of an aperture ratio.

In the second embodiment, since the "phenomenon in which SNR decreases" is also considered, a parameter called image quality (FOM) is defined using the visibility of the first embodiment as in the following expression. Note that when D=1, standardization is performed such that FOM=1.

$$FOM = V\_m \times MTF\_Dn \times SNR \qquad \text{Expression (7)}$$

As in the first embodiment, in the case where an amount of X-rays with which the detector 106 is irradiated at the time of exposure does not decrease when the aperture ratio of the first shield grating portion 105b is decreased, SNR=1. Here, the visibility of a detection result defined in the first embodiment=FOM.

In the second embodiment, since only quantum noise is treated as noise, the SNR depends only on aperture ratio D of the first shield grating portion 105b and expressed as Expression (8) below.

$$SNR = \sqrt{D} \qquad \text{Expression (8)}$$

In accordance with Expressions (5), (7), and (8), Expression (9) below is calculated.

$$FOM = V\_m \times \frac{\sin(D \times m \times ps/2n)}{D \times m \times ps/2n} \times \sqrt{D} \qquad \text{Expression (9)}$$

In addition, when a moiré pattern is expressed as Expression (2), Expression (10) below is calculated.

$$FOM = \frac{m}{\pi D} \sin\frac{\pi D}{m} \times \frac{\sin(D \times m \times ps/2n)}{D \times m \times ps/2n} \times \sqrt{D} \qquad \text{Expression (10)}$$

Figure 6A:
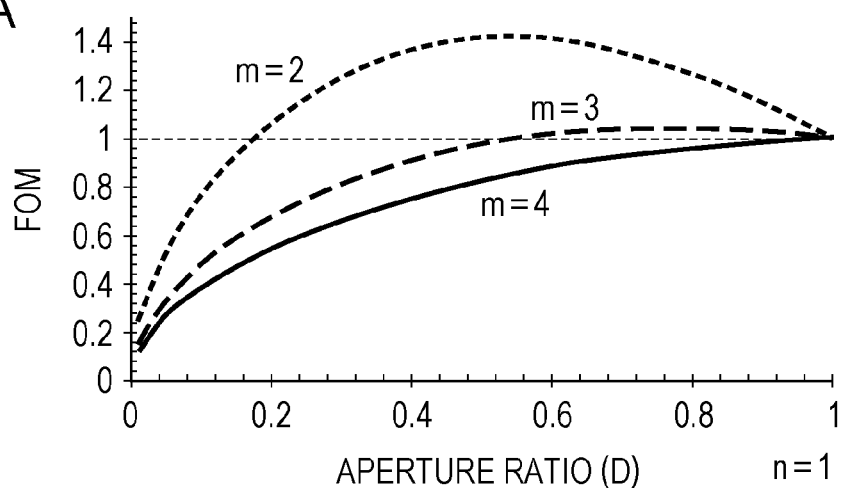
FIG. 6A is a graph illustrating a relationship between FOM of a detection result and the aperture ratio of the first shield grating portion according to the second embodiment.

Results of calculation of FOM obtained by substituting n=1 and m=2, 3, and 4 into Expression (10) are illustrated in FIG. 6A. In FIG. 6A, on the condition that the amount of X-rays with which the inspection object 103 is irradiated is constant, as a result of decreasing of the aperture ratio, there are a case where FOM is improved (FOM>1) and a case where FOM is decreased (FOM<1). In the second embodiment, in order to realize FOM>1, a condition expressed as Expression (11) below is obtained from FIG. 6A.

$$1/3 \leq n/m \qquad \text{Expression (11)}$$

When n/m<1/3, the decrease in SNR affects FOM more significantly than or at the same level as the improvement in visibility caused by the decrease in the aperture ratio.

In contrast, in the case where information on the inspection object 103 is calculated using a Fourier transform method from a detection result in the arithmetic unit 203, the Nyquist frequency is reached at n/m=1/2. Thus, a folding phenomenon occurs at n/m>1/2 when sampling is performed, and it may be incapable of faithfully reproducing information on the inspection object 103 from a calculation result (the accuracy of a calculation result is decreased). Accordingly, in the case where information on the inspection object 103 is calculated using a Fourier transform method from a detection result in the arithmetic unit 203, Expression (12) below is a necessary condition.

$$1/3 \leq n/m \leq 1/2 \qquad \text{Expression (12)}$$

Figure 6B:
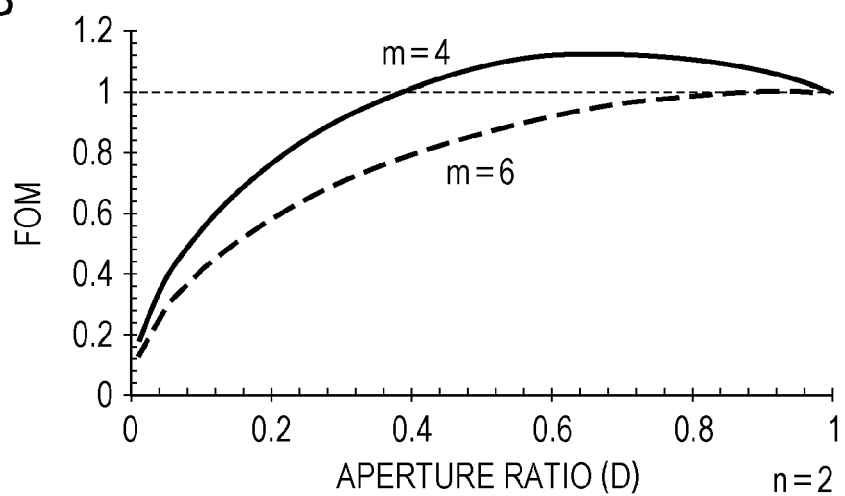
FIG. 6B is a graph illustrating a relationship between FOM of a detection result and the aperture ratio of the first shield grating portion according to the second embodiment.
Figure 6C:
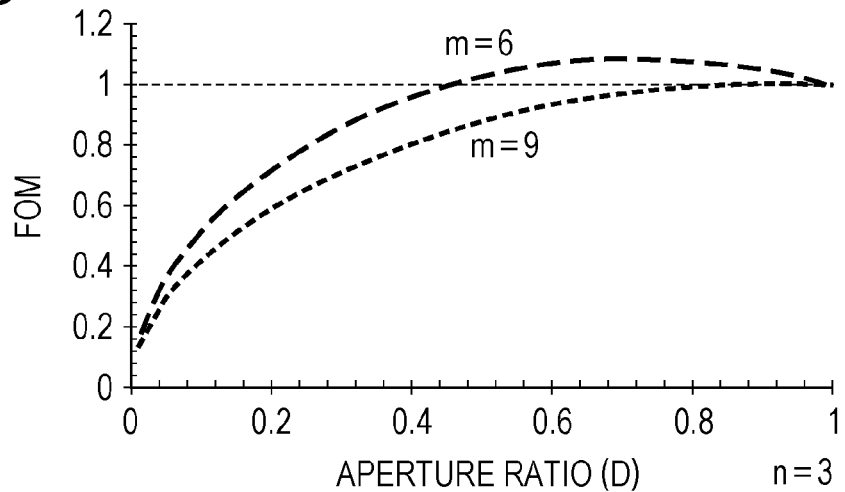
FIG. 6C is a graph illustrating a relationship between FOM of a detection result and the aperture ratio of the first shield grating portion according to the second embodiment.

In FIG. 6A, the aperture ratio that satisfies FOM>1 is 0.2<D<1 when n=1 and m=2, and 0.65<D<1 when n=1 and m=3. In accordance with FIG. 6A and Expression (9), since the FOM does not become 1 or more when n=1 and m=4, results obtained when n=2 are illustrated in FIG. 6B. When n=2, as illustrated in FIG. 5B, since a transmissive portion 125b of the first shield grating portion 105b is arranged in units of two pixels, it is possible to measure a fringe period with higher accuracy when m=4 than when n=1. This is because, even in a pattern the period of which is identical (m=4), MTF_D is significantly increased by virtually increasing a pixel size of the detector 106. In FIG. 6B, in the case where n=2 and m=4, the FOM becomes 1 or more when 0.4<D<1. However, in the case where n=3, a calculation result exceeds the Nyquist frequency when m=4 (n/m=3/4>1/2). Thus, in the case where information on the inspection object 103 is calculated using a Fourier transform method from a detection result, the accuracy of a calculation result is decreased. Since an optimal fringe period obtained when n=3 is 6≤m≤9, results of calculation of FOM obtained by substituting m=6 and 9 when n=3 are illustrated in FIG. 6C. In FIG. 6C, in the case where n=3 and m=6, the FOM becomes 1 or more when 0.45<D<1. In the case where n=3 and m=9, the FOM becomes 1 or more when 0.85<D<1. In this manner, in the case where the amount of X-rays with which the pixels 107 are irradiated decreases with a decrease in the aperture ratio of the first shield grating portion 105b, the aperture ratio (D) and period/pixel size of the first shield grating portion 105b need to be changed in accordance with the period/pixel size of a periodic pattern on the detector 106. Note that, in order to have a better effect in improving FOM, it is desirable that 0.25<D<0.9 when n=1 and m=2 and 0.6<D<0.8 when n=2 and m=4. In such a range, the FOM becomes 1.1 or more.

Figure 7A:
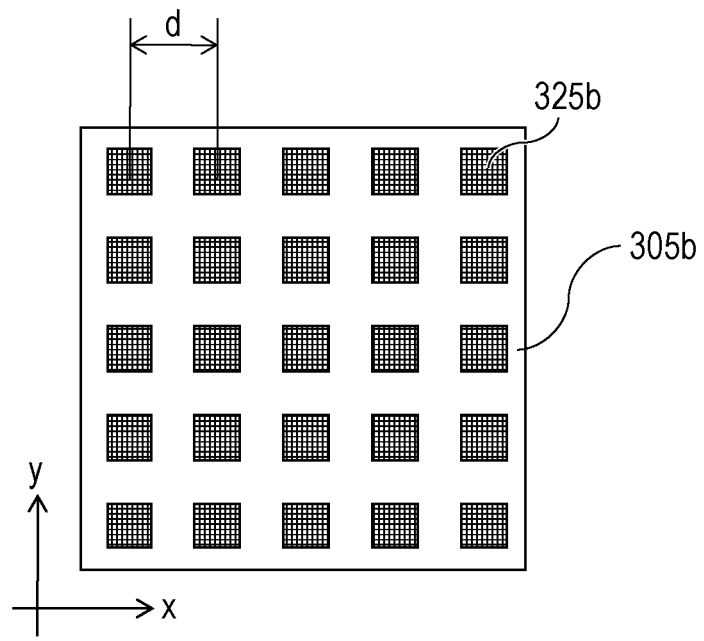
FIG. 7A is a schematic diagram of a second grating according to the second embodiment.

In contrast, in the case where a two-dimensional grating that has periods in two directions (the x direction and the y direction) as illustrated in FIG. 7A is used as a first shield grating portion 305b, the dependence of SNR on aperture ratio becomes more significant than in the case where a one-dimensional grating is used. The SNR obtained when the first shield grating portion 305b is a two-dimensional grating is expressed as Expression (13) below.

$$SNR = \sqrt{Dx} \times \sqrt{Dy} \qquad \text{Expression (13)}$$

Note that Dx denotes the aperture ratio of the first shield grating portion 305b in the x direction and the width of a transmissive portion 325b in the first period A in the x direction. Dy denotes the aperture ratio of the first shield grating portion 305b in the y direction and the width of the transmissive portion 325b in the first period A in the y direction. In the case of a two-dimensional grating, the SNR obtained when Dx (the aperture ratio in the x direction)=Dy (the aperture ratio in the y direction)=0.5 is about 50% lower than the SNR obtained when Dx=Dy=(there is no first shield grating portion 305b). Likewise, the SNR obtained when Dx=Dy=0.25 is 75% lower than the SNR obtained when Dx=Dy=1. When the first shield grating portion 305b is a two-dimensional grating, Expressions (14 ((14a) and (14b))) are calculated in accordance with Expressions (5), (7), and (13). Note that FOM in the x direction is denoted by FOMx, FOM in the y direction is denoted by FOMy, V_m (the visibility of the moiré pattern 109) in the x direction is denoted by V_m$_x$, V_m in the y direction is denoted by V_m$_y$, m in the x direction is denoted by m_x, m in the y direction is denoted by m_y, n in the x direction is denoted by n_x, and n in the y direction is denoted by n_y.

$$FOMx = V\_m_x \times \frac{\sin\left(Dx \times m\_x \times \frac{ps}{2n\_x}\right)}{Dx \times m\_x \times \frac{ps}{2n\_x}} \times \sqrt{Dx} \times \sqrt{Dy} \qquad \text{Expression (14a)}$$

$$FOMy = V\_m_y \times \frac{\sin\left(Dy \times m\_y \times \frac{ps}{2n\_y}\right)}{Dy \times m\_y \times \frac{ps}{2n\_y}} \times \sqrt{Dx} \times \sqrt{Dy} \qquad \text{Expression (14b)}$$

When the moiré pattern 109 is expressed as Expression (2), Expressions (15 ((15a) and (15b))) below are calculated.

$$FOMx = \frac{m\_x}{\pi Dx} \sin\frac{\pi Dx}{m\_x} \times \frac{\sin(Dx \times m\_x \times ps/2n\_x)}{Dx \times m\_x \times ps/2n\_x} \times \sqrt{Dx} \times \sqrt{Dy} \qquad \text{Expression (15a)}$$

$$FOMy = \frac{m\_y}{\pi Dy} \sin\frac{\pi Dy}{m\_y} \times \frac{\sin(Dy \times m\_y \times ps/2n\_y)}{Dy \times m\_y \times ps/2n\_y} \times \sqrt{Dx} \times \sqrt{Dy} \qquad \text{Expression (15b)}$$

Figure 7B:
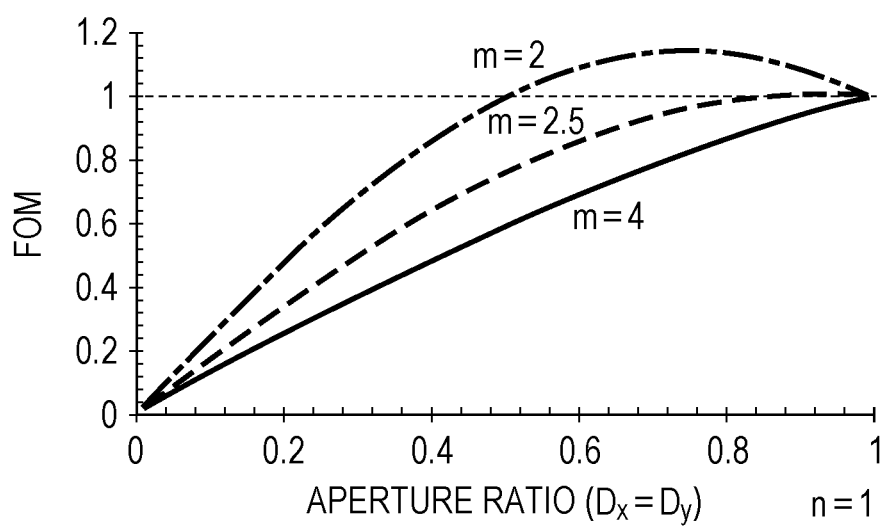
FIG. 7B is a graph illustrating a relationship between FOM of a detection result and the aperture ratio of the first shield grating portion.

Results of calculation of FOM obtained by substituting n_x=n_y=1 and m_x=m_y=2, 3, and 4 into Expressions (15) are illustrated in FIG. 7B. Note that the aperture ratio Dx=Dy. In comparison with the one-dimensional grating illustrated in FIG. 6A, the range of √(n_x×n_y/m_x×m_y) that satisfies FOM>1 becomes smaller and the maximum value of FOM becomes also smaller. However, it is clear that the second embodiment has an advantageous effect even when the first shield grating portion 305b is a two-dimensional grating. Note that an effective range of n/m is expressed as Expression (16) below.

$$1/2.5 \leq \sqrt{(n\_x \times n\_y / m \times m\_y)} \leq 1/2 \quad \text{Expression (16)}$$

Note that, even in the second embodiment, similarly to as in the first embodiment, the first shield grating portion 305b and a second shield grating portion may be integrally formed or formed independently from each other. In addition, in the case where it is impossible to make the distance between the first shield grating portion 305b and the detector 106 be 0, periods $A_x$ and $A_y$ of the first shield grating portion 305b need to be corrected using the following expressions.

$$A_x = ps_x \times n_x \times \frac{Ls}{Ls + Lf}$$
$$A_y = ps_y \times n_y \times \frac{Ls}{Ls + Lf}$$

Note that $A_x$ denotes a first period in the x direction, $ps_x$ denotes a pixel size in the x direction, and $n_x$ denotes the first period/the pixel size ($A_x/ps_x$) in the x direction. Likewise, $A_y$ denotes the first period in the y direction, $ps_y$ denotes the pixel size in the y direction, and $n_y$ denotes the first period/the pixel size ($A_y/ps_y$) in the y direction.

Although the case where the moiré pattern 109 is formed on the detector 106 has been described in the second embodiment, the second embodiment may also be similarly applied to a case where a periodic pattern other than a moiré pattern is formed.

In addition, in the case where information on an inspection object is obtained without performing calculation (for example, a case where a detection result is simply changed into an image and the image is displayed on an image display portion) and in the case where information on an inspection object is calculated from a detection result without using a Fourier transform method, there is no need to consider the Nyquist frequency. Thus, conditions that satisfy FOM>1 become less restricted.

Exemplary Embodiment 1

In an exemplary embodiment 1, a detailed exemplary embodiment of the first embodiment will be described. In the exemplary embodiment 1, an X-ray generator using a rotating anticathode composed of tungsten is used as the X-ray source 101. The X-rays 102, which are diverging X-rays, are generated from the X-ray source 101 and enter the first grating 104, the second grating 105, and the detector 106 in this order. The second grating 105 is configured such that the first shield grating portion 105b and the second shield grating portion 105a are integrally formed as illustrated in FIG. 2A. In addition, suppose that when n=1, an amount of X-rays with which the pixels of the detector 106 are irradiated is constant regardless of the aperture ratio D of the first shield grating portion 105b.

Suppose that the first grating 104 has a one-dimensional stripe-shaped pattern the period of which is 10 μm and an amount of phase modulation is 1/2 times a wavelength of 0.35 Å. Since the size of the pixels 107 of the detector 106 is 50 μm, the first period A of the first shield grating portion 105b is 50 μm. A direction 111 of the first period A matches one of directions in which the pixels 107 of the detector 106 are two-dimensionally arranged. Suppose that the distance from the X-ray source 101 to the first grating 104 is 90 cm, the distance from the first grating 104 to the first shield grating portion 105b is 58 cm, and the distance between the first shield grating portion 105b and the detector 106 is 0 cm. The second period B of the second shield grating portion 105a varies depending on the period of a moiré pattern 109 desired to be formed and a method for forming a moiré pattern (an enlarged or reduced moiré pattern or a rotation moiré pattern).

When the period of a self-image formed on the second shield grating portion 105a by the first grating 104 is 8.24 μm and the period of the moiré pattern 109 desired to be formed is 200 μm, a case where an enlarged or reduced moiré pattern is formed (FIG. 8A) and a case where a rotation moiré pattern is formed (FIG. 8B) will be briefly described.

In FIGS. 8A and 8B, the moiré pattern 109 is formed by using a self-image 108 formed on the second grating 105 and the second shield grating portion 105a of the second grating 105 in combination. It is desirable that a direction 113 of the period of the moiré pattern 109 (hereinafter simply referred to as a moiré period direction 113) be parallel to the direction 111 of the first period A of the first shield grating portion 105b (an angle of 0 degrees).

In the case where an enlarged or reduced moiré pattern is formed, a direction 114 of the period of the self-image 108 (hereinafter simply referred to as a self-image period direction 114), a direction 112 of the second period B, and the moiré period direction 113 are parallel to one another. Thus, when the moiré period direction 113 and the direction 111 of the first period A of the first shield grating portion 105b are made to be parallel to each other (an angle of 0 degrees), the direction 111 of the first period A is parallel to the direction 112 of the second period B.

In contrast, in the case where a rotation moiré pattern is formed, the self-image period direction 114, the direction 112 of the second period B, and the moiré period direction 113 intersect with one another (not parallel to one another). Thus, when the moiré period direction 113 and the direction 111 of the first period A of the first shield grating portion 105b are made to be parallel to each other (an angle of 0 degrees), the direction 111 of the first period A intersects with the direction 112 of the second period B at an angle of θβ (FIG. 8B). Here, the self-image period direction 114 intersects with the direction 111 of the first period A at an angle of θα.

Table 1 shows the second period B, the angle (θα−θβ) formed by the self-image period direction 114 and the direction 112 of the second period B, the angle (θα) formed by the self-image period direction 114 and the direction 111 of the first period A, and the angle (θβ) formed by the direction 111 of the first period A and the direction 112 of the second period B in the case where the moiré pattern 109 is formed as illustrated in FIGS. 8A and 8B.

TABLE 1

| | Angle formed by moiré pattern and first period | Second period | Angle (θα − θβ) formed by self-image and second period | Angle (θα) formed by self-image and first period | Angle (θβ) formed by first period and second period |
|---|---|---|---|---|---|
| Enlarged or reduced moiré pattern | 0 degrees (parallel) | 8.59 μm or 7.92 μm | 0 degrees (parallel) | 0 degrees (parallel) | 0 degrees (parallel) |
| Rotation moiré pattern | 0 degrees (parallel) | 8.24 μm | 2.36 degrees | 91.18 degrees | 88.82 degrees |

In this manner, the direction 112 of the second period B of the second shield grating portion 105a for forming an enlarged or reduced moiré pattern differs from that of the second period B of the second shield grating portion 105a for forming a rotation moiré pattern by about 90 degrees. In addition, the second period B of the second shield grating portion 105a for forming an enlarged or reduced moiré pattern also differs from that of the second shield grating portion 105a for forming a rotation moiré pattern. Thus, it is determined which of the methods is to be used to form a moiré pattern at the stage of fabricating the second grating 105. In addition, depending on a method for forming a moiré pattern, it is necessary to adjust the angle formed by the direction 111 of the first period A and the direction 112 of the second period B.

In the exemplary embodiment 1, as illustrated in FIG. 4, the smaller the aperture ratio, the higher the visibility of a detection result. However, the smaller the aperture ratio, the smaller the amount of X-rays with which the pixels 107 of the detector 106 are irradiated per unit time. Thus, the smaller the aperture ratio, the longer the exposure time. Accordingly, the aperture ratio of the first shield grating portion 105b needs to be determined by taking the balance between the exposure time and the visibility of a detection result into consideration.

Exemplary Embodiment 2

In an exemplary embodiment 2, a detailed exemplary embodiment of the second embodiment will be described. In the exemplary embodiment 2, the configuration of an X-ray Talbot interferometer is similar to that of the exemplary embodiment 1 except for the first period A. Note that it is assumed that, unlike in the exemplary embodiment 1, the inspection object 103 is irradiated with a constant amount of X-rays regardless of the aperture ratio of the first shield grating portion 105b in the exemplary embodiment 2. The amount of X-rays with which the detector 106 is irradiated is proportional to the aperture ratio of the first shield grating portion 105b. Thus, in the exemplary embodiment 2, it is necessary to consider the relationship between the aperture ratio D of the first shield grating portion 105b and SNR. In the case where the first period A is 100 μm (n=2), the FOM becomes greatest when the aperture ratio D is 2/3 as illustrated in FIG. 6B in the exemplary embodiment 2. In addition, the aperture ratio D that satisfies FOM>1 is 0.4<D<1. When 0.55≤D≤0.85, the FOM is 10% or more higher than that in the case where D=1. Unlike in the exemplary embodiment 1, since the amount of X-rays with which the inspection object 103 is irradiated is constant regardless of the aperture ratio D, an exposure time does not change even when the aperture ratio is changed.

Exemplary Embodiment 3

In an exemplary embodiment 3, a detailed exemplary embodiment of the second embodiment will be described. The exemplary embodiment 3 differs from the exemplary embodiment 2 in that, in the exemplary embodiment 3, each of the first grating 104 and first and second shield grating portions of the second grating 105 is a two-dimensional grating that has periods in two directions. Similarly to as in the exemplary embodiment 2, the inspection object 103 is irradiated with a constant amount of X-rays regardless of the aperture ratio of a first shield grating portion 305 of the second grating 105.

Suppose that the first grating 104 has a checkerboard pattern the period of which is 10 μm and an amount of phase modulation is 1/2 times a wavelength of 0.35 Å. Since the size of the pixels 107 of the detector 106 is 50 μm, the first period A of the first shield grating portion 305 is set to 50 μm (n_x=n_y=1). The direction 111 of the first period A matches the orientation in which the pixels 107 of the detector 106 are two-dimensionally arranged. Suppose that the distance from the X-ray source 101 to the first grating 104 is 90 cm, the distance from the first grating 104 to the first shield grating portion 305 is 58.2 cm, and the distance between the first shield grating portion 305 and the detector 106 is 0 cm.

Also in the case where each grating is a two-dimensional grating, similarly to as in the case where each grating is a one-dimensional grating, examples of a method for forming a moiré pattern include a method for forming an enlarged or reduced moiré pattern and a method for forming a rotation moiré pattern. When the period of the self-image 108 formed on the first shield grating portion 305 by the first grating 104 is 8.24 μm and the period of the moiré pattern 109 desired to be formed is 100 μm, a case where an enlarged or reduced moiré pattern is formed (FIG. 9A) and a case where a rotation moiré pattern is formed (FIG. 9B) will be briefly described.

Figure 9A:
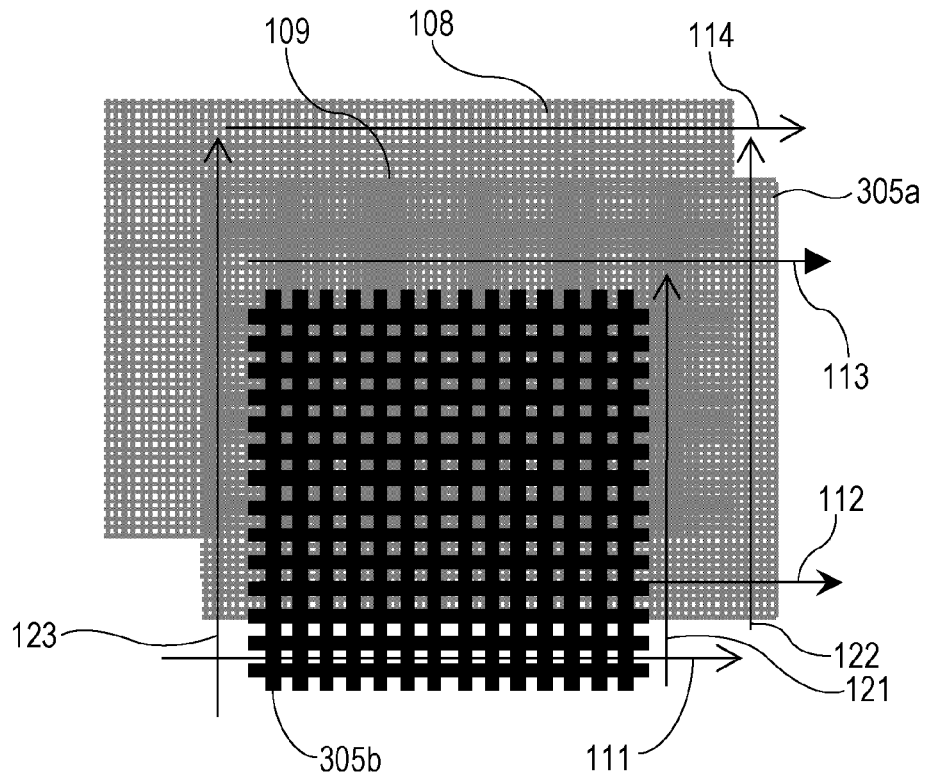
FIG. 9A is a schematic diagram of an interference pattern, a moiré pattern, and directions of the period of the second grating associated with an exemplary embodiment 3 of the present invention.
Figure 9B:
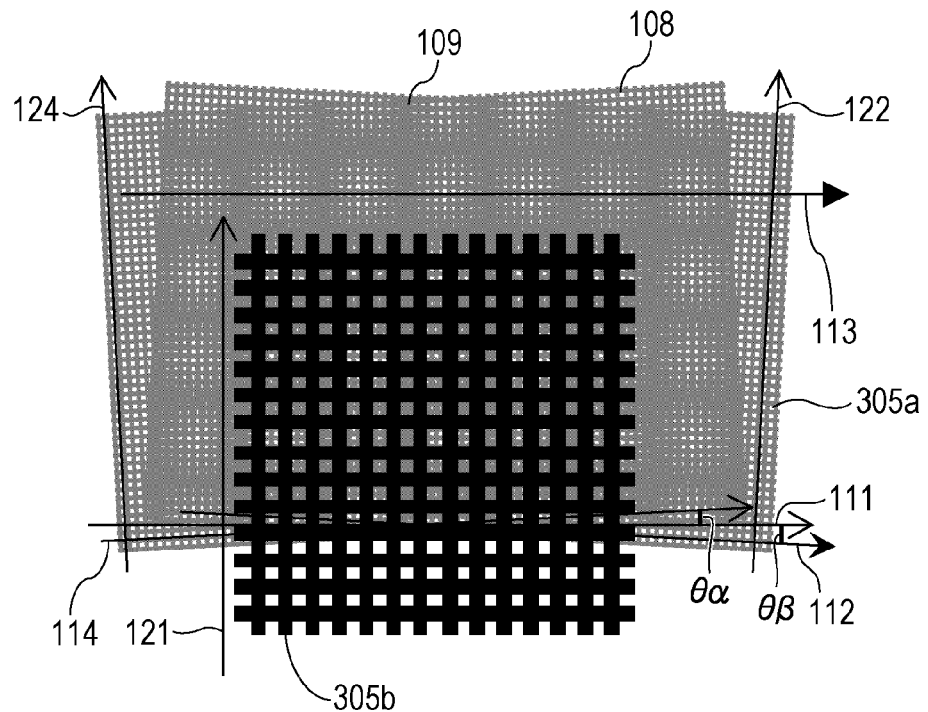
FIG. 9B is a schematic diagram of an interference pattern, a moiré pattern, and directions of the period of the second grating associated with the exemplary embodiment 3 of the present invention.

Similarly to as in the exemplary embodiment 1, in FIGS. 9A and 9B, the moiré pattern 109 is formed by using the self-image 108 formed on the second grating 105 and a second shield grating portion 305a of the second grating 105 in combination. It is desirable that the moiré period direction 113 be parallel to the direction 111 of the first period A of the first shield grating portion 305 and a direction 123 of the period of the moiré pattern 109 be parallel to a direction 121 of the first period A of the first shield grating portion 305. Thus, in the case where an enlarged or reduced moiré pattern is formed, the directions 111 and 121 of the first period A are parallel to the directions 112 and 122 of the second period B, respectively. In contrast, in the case where a rotation moiré pattern is formed, the directions 111 and 121 of the first period A intersect with the directions 112 and 122 of the second period B, respectively, at an angle of θβ. Here, the self-image period direction 114 intersects with the direction 111 of the first period A at an angle of θα and a direction 124 of the period of the self-image 108 (hereinafter simply referred to as a self-image period direction 124) intersects with the direction 121 of the first period A at an angle of θα.

Table 2 shows the second period B, the angle (θα−θβ) formed by the self-image period directions 114 and 124 and the directions 112 and 122 of the second period B, the angle (θα) formed by the self-image period directions 114 and 124 and the directions 111 and 121 of the first period A, and the angle (θβ) formed by the directions 111 and 121 of the first period A and the directions 112 and 122 of the second period B, in the case where the moiré pattern 109 is formed as illustrated in FIGS. 9A and 9B.

TABLE 2

| | Angle formed by moiré pattern and first period | Second period | Angle (θα – θβ) formed by self-image and second period | Angle (θα) formed by self-image and first period | Angle (θβ) formed by first period and second period |
|---|---|---|---|---|---|
| Enlarged or reduced moiré pattern | 0 degrees (parallel) | 8.98 μm or 7.61 μm | 0 degrees (parallel) | 0 degrees (parallel) | 0 degrees (parallel) |
| Rotation moiré pattern | 0 degrees (parallel) | 8.24 μm | 4.72 degrees | 2.36 degrees | −2.36 degrees |

In this manner, the direction 112 of the second period B of the second shield grating portion 305a for forming an enlarged or reduced moiré pattern differs from that of the second period B of the second shield grating portion 305a for forming a rotation moiré pattern by about a few degrees. In addition, the second period B of the second shield grating portion 305a for forming an enlarged or reduced moiré pattern also differs from that of the second shield grating portion 305a for forming a rotation moiré pattern. Thus, it is determined which of the methods is to be used to form a moiré pattern at the stage of fabricating the second grating 105. In addition, depending on a method for forming a moiré pattern, it is necessary to adjust the angle formed by the direction 111 of the first period A and the direction 112 of the second period B and the angle formed by the direction 121 of the first period A and the direction 122 of the second period B.

In the case where $n_x=n_y=1$, the FOM becomes greatest when both the aperture ratios $D_x$ and $D_y$ are 3/4 as illustrated in FIG. 7B in the exemplary embodiment 3. In addition, the aperture ratios $D_x$ and $D_y$ that satisfy FOM>1 are $0.5<D_x<1$ and $0.5<D_y<1$. When $0.65 \leq D_x \leq 0.85$ and $0.65 \leq D_y \leq 0.85$, the FOM is 10% or more higher than that in the case where $D_x=D_y=1$. Unlike in the exemplary embodiment 1, since the amount of X-rays with which the inspection object 103 is irradiated is constant regardless of the aperture ratio, an exposure time does not change even when the aperture ratio is changed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-049349, filed Mar. 12, 2013, which is hereby incorporated by reference herein in its entirety.

What is claimed is:

1. An X-ray Talbot interferometer comprising:
a first grating configured to diffract X-rays from an X-ray source and to form an interference pattern;
a second grating configured to block a portion of X-rays that form the interference pattern; and
a detector configured to detect X-rays from the second grating, wherein a property of an inspection object disposed between the X-ray source and the second grating is measured,
wherein the second grating includes
a first shield grating portion in which a shield portion and a transmissive portion are arranged periodically at a first period and
a second shield grating portion in which a shield portion and a transmissive portion are arranged periodically at a second period, and
the first period is expressed as follows:

$$ps \times n \times \frac{Ls}{Ls + Lf}$$

where ps denotes a size of pixels that the detector has, n denotes a positive integer, Ls denotes a distance from the X-ray source to the first shield grating portion, and Lf denotes a distance from the first shield grating portion to the detector.

2. The X-ray Talbot interferometer according to claim 1, wherein the first shield grating portion is a one-dimensional grating that has a period in a direction of the first period,
a period of a periodic pattern formed on the detector is m times the size of the pixels,
the first period is n times the size of the pixels,
visibility of the periodic pattern is denoted by V_m,
an aperture ratio of the first shield grating portion is denoted by D, and
the size of the pixels is denoted by ps, and
when the inspection object is measured, in a case where SNR=1 when an amount of X-rays with which the detector is irradiated is constant regardless of the aperture ratio and SNR=√D when an amount of X-rays with which the detector is irradiated changes with the aperture ratio, the following expression is satisfied:

$$V\_m \times \frac{\sin(D \times m \times ps/2n)}{D \times m \times ps/2n} \times SNR > 1.$$

3. The X-ray Talbot interferometer according to claim 1, wherein the first shield grating portion is a two-dimensional grating that has periods in an x direction and in a y direction, the x and y directions intersecting with each other,
a period of a periodic pattern formed on the detector in the x direction is $m_x$ times the size of the pixels,
a period of the periodic pattern formed on the detector in the y direction is $m_y$ times the size of the pixels,
a period of the first shield grating portion in the x direction is $n_x$ times the size of the pixels,
a period of the first shield grating portion in the y direction is $n_y$ times the size of the pixels,
visibility of the periodic pattern in the x direction is denoted by $V\_m_x$,
visibility of the periodic pattern in the y direction is denoted by $V\_m_y$,
an aperture ratio of the first shield grating portion in the x direction is denoted by $D_x$,
an aperture ratio of the first shield grating portion in the y direction is denoted by $D_y$, and
the size of the pixels is denoted by ps, and
when the inspection object is measured, in a case where SNR=1 when an amount of X-rays with which the detector is irradiated is constant regardless of the aperture ratio and SNR=√$D_x$×√$D_y$ when an amount of X-rays with which the detector is irradiated changes with the aperture ratio, then one or more of the expressions below are satisfied:

$$V\_m_x \times \frac{\sin\left(Dx \times m\_x \times \frac{ps}{2n\_x}\right)}{Dx \times m\_x \times \frac{ps}{2n\_x}} \times SNR > 1$$

$$V\_m_y \times \frac{\sin\left(Dy \times m\_y \times \frac{ps}{2n\_y}\right)}{Dy \times m\_y \times \frac{ps}{2n\_y}} \times SNR > 1.$$

4. The X-ray Talbot interferometer according to claim 1, wherein the first shield grating portion is a one-dimensional grating that has a period in a direction of the first period, and in a case where a period of a periodic pattern formed on the detector is m times the size of the pixels and the first period is n times the size of the pixels, the following expression is satisfied:

$1/3 \leq n/m \leq 1/2$.

5. The X-ray Talbot interferometer according to claim 1, wherein the first shield grating portion is a two-dimensional grating that has periods in an x direction and in a y direction, the x and y directions intersecting with each other, and in a case where a period of a periodic pattern formed on the detector in the x direction is $m_x$ times the size of the pixels, a period of the periodic pattern formed on the detector in the y direction is $m_y$ times the size of the pixels, a period of the first shield grating portion in the x direction is $n_x$ times the size of the pixels, and a period of the first shield grating portion in the y direction is $n_y$ times the size of the pixels, the following expression is satisfied:

$1/2.5 \leq \sqrt{(n\_x \times n\_y / m x \times m\_y)} \leq 1/2$.

6. The X-ray Talbot interferometer according to claim 1, wherein the first shield grating portion is a one-dimensional grating that has a period in a direction of the first period, and the direction of the first period intersects with a direction of the second period.

7. The X-ray Talbot interferometer according to claim 1, wherein the first shield grating portion is a two-dimensional grating that has periods in an x direction and in a y direction, the x and y directions intersecting with each other, and the x direction, the y direction, and a direction of the second period intersect with one another.

8. The X-ray Talbot interferometer according to claim 1, wherein each of the first shield grating portion and the second shield grating portion is a shield grating, and the first shield grating portion and the second shield grating portion are formed independently from each other.

9. The X-ray Talbot interferometer according to claim 2, wherein the first shield grating portion is the one-dimensional grating that has a period in the direction of the first period, and in a case where the period of the periodic pattern formed on the detector is m times the size of the pixels and the first period is n times the size of the pixels, the following expression is satisfied:

$1/3 \leq n/m \leq 1/2$.

10. The X-ray Talbot interferometer according to claim 3, wherein the first shield grating portion is the two-dimensional grating that has periods in the x direction and in the y direction, the x and y directions intersecting with each other, and in a case where the period of the periodic pattern formed on the detector in the x direction is $m_x$ times the size of the pixels, the period of the periodic pattern formed on the detector in the y direction is $m_y$ times the size of the pixels, the period of the first shield grating portion in the x direction is $n_x$ times the size of the pixels, and the period of the first shield grating portion in the y direction of the first shield grating portion is $n_y$ times the size of the pixels, the following expression is satisfied:

$1/2.5 \leq \sqrt{(n\_x \times n\_y / m x \times m\_y)} \leq 1/2$.

11. The X-ray Talbot interferometer according to claim 2, wherein the first shield grating portion is a one-dimensional grating that has a period in a direction of the first period, and the direction of the first period intersects with a direction of the second period.

12. The X-ray Talbot interferometer according to claim 4, wherein the first shield grating portion is the one-dimensional grating that has a period in the direction of the first period, and the direction of the first period intersects with a direction of the second period.

13. The X-ray Talbot interferometer according to claim 3, wherein the first shield grating portion is the two-dimensional grating that has periods in the x direction and in the y direction, the x and y directions intersecting with each other, and the x direction, the y direction, and a direction of the second period intersect with one another.

14. The X-ray Talbot interferometer according to claim 5, wherein the first shield grating portion is the two-dimensional grating that has periods in the x direction and in the y direction, the x and y directions intersecting with each other, and the x direction, the y direction, and a direction of the second period intersect with one another.

15. The X-ray Talbot interferometer according to claim 2, wherein each of the first shield grating portion and the second shield grating portion is a shield grating, and the first shield grating portion and the second shield grating portion are formed independently from each other.

16. An X-ray imaging system comprising:

the X-ray Talbot interferometer according to claim 1; and an arithmetic unit configured to calculate information on the inspection object on the basis of a detection result of the detector that the X-ray Talbot interferometer has.

17. An X-ray imaging system comprising:

the X-ray Talbot interferometer according to claim 2; and an arithmetic unit configured to calculate information on the inspection object on the basis of a detection result of the detector that the X-ray Talbot interferometer has.

* * * * *